United States Patent [19]
Danby et al.

[11] Patent Number: 5,206,522
[45] Date of Patent: Apr. 27, 1993

[54] DEVICE FOR DETECTING AIR IN FLUID CONDUCTING TUBING

[75] Inventors: Hal C. Danby, Sudbury; Alan Brundle, Halstead, both of United Kingdom

[73] Assignee: Danby Medical Limited, Earls Colne, United Kingdom

[21] Appl. No.: 775,449

[22] Filed: Oct. 15, 1991

[30] Foreign Application Priority Data

Oct. 17, 1990 [GB] United Kingdom ............... 9022479

[51] Int. Cl.⁵ .................................... G01N 15/06
[52] U.S. Cl. .................................... 250/574; 604/122
[58] Field of Search ............. 250/573, 574, 576, 564; 356/339, 440, 441, 442; 128/DIG. 13; 604/122, 67, 253, 123; 340/627, 632, 634

[56] References Cited

U.S. PATENT DOCUMENTS

| | | |
|---|---|---|
| 3,544,798 | 12/1970 | Topol . |
| 4,227,814 | 10/1980 | Soodak et al. ............... 250/576 |
| 4,319,138 | 3/1982 | Sweet ............................ 250/576 |
| 4,857,050 | 8/1989 | Lentz et al. .................. 604/122 |
| 4,884,065 | 11/1989 | Crouse et al. ............. 128/DIG. 13 |
| 5,102,392 | 4/1992 | Sakai et al. ............... 128/DIG. 13 |

FOREIGN PATENT DOCUMENTS

| | | |
|---|---|---|
| 0050812 | 5/1982 | European Pat. Off. . |
| 0121848 | 10/1984 | European Pat. Off. . |
| 0199919 | 11/1986 | European Pat. Off. . |
| 0209659 | 1/1987 | European Pat. Off. . |
| 0238809 | 9/1987 | European Pat. Off. . |
| 0289833 | 11/1988 | European Pat. Off. . |
| 1254708 | 11/1971 | United Kingdom . |

Primary Examiner—David C. Nelms
Assistant Examiner—K. Shami
Attorney, Agent, or Firm—Oblon, Spivak, McClelland, Maier & Neustadt

[57] ABSTRACT

A device for detecting air in large bore thin walled transparent tubing, including a body providing accommodation for the tubing; an LED in a passage body for transmitting light energy towards the tubing; a phototransistor mounted in an orthogonally extending passage for receiving light transmitted by LED and modified by changes in the constituency of fluid passing through tubing; and an optical spacer in the form of a slotted collar of material optically matched to the material of tubing occupying space between LED and the tubing and phototransistor.

25 Claims, 1 Drawing Sheet

DEVICE FOR DETECTING AIR IN FLUID CONDUCTING TUBING

BACKGROUND OF THE INVENTION

1. Field of the Invention

This invention relates to devices and arrangements for detecting air or air bubbles in fluid conducting tubing and in particular in fluid conducting tubing forming part of a fluid flow system utilized for the intravenous supply of fluid to a medical patient.

2. Discussion of Background

Typically transparent walled p.v.c. tubing is employed in systems as last-mentioned because it is hygienic and cheap—it being common practice to change and discard the length of tubing in use frequently.

A known arrangement for use in clinical analysis and capable of detecting air in tubing utilizes a device as illustrated in transverse section in FIG. 1 of the accompanying drawings.

Referring to FIG. 1, the known device includes a body—member 1 having a passage 2 passing therethrough in which may be accommodated a length of transparent walled p.v.c. tubing 3. Passage 2 is open at the top (as viewed) in order that the tubing 3 may readily be slotted into position and of course removed after use. Extending into the body 1 from its base and right-hand side (as viewed) respectively are two circular-cylindrical passages 4 and 5 which are orthogonal to each other and exit via apertures 6, 7 respectively into tubing passage 2.

Located in circular cylindrical passage 4 is an infrared receiver 8 (a phototransistor) which receives infra-red energy transmitted by an infra-red transmitter 9 (an LED).

In operation the output level of receiver 8 depends upon the nature of the fluid passing through the tubing 3 past receiver 8 and transmitter 9. Different fluids will result in different output levels with a significant change if air is present. For example, in a test a voltmeter 10 connected to the output of a suitable detector circuit 11 was found to indicate 0.1 volts when the fluid passing through tubing 3 was distilled water; 0.2 volts when the fluid was semi-skimmed milk; 1.4 volts when the fluid was a 20% intralipid solution and 4.2 volts when air passed through.

Whilst not a primary function of a clinical analyzer, a device as shown in FIG. 1 will therefore operate as a detector of air passing through tubing 3. However, as is represented, p.v.c. tubing typically used in a clinical analyzer is small bore thick-walled tubing with an outside diameter of 2.5 mm and an inside diameter of 0.9 mm. In the intravenous supply of fluids to a patient however the standard p.v.c. tubing used is of relatively large bore and thin walled having an outside diameter of 4 mm and an inside diameter of 3.1 mm.

SUMMARY OF THE INVENTION

Accordingly, one object of the present invention is to provide an improved arrangement for detecting air-in-line in a fluid conducting system as referred to above. Towards that end, experiments have been carried out in connection with the detection of air-in-line with a device generally as illustrated in FIG. 1, but adapted dimensionally to accept the relatively large bore, thin walled tubing utilized for the intravenous supply of fluid to a patient but the results achieved were not satisfactory. Particularly bearing in mind the critical importance of detecting "air-in-line" in such applications, the changes that took place in the output of the receiver corresponding to receiver 8 in FIG. 1 were insufficiently marked for the device to be regarded as useful in this connection.

However, further experimentation led to the introduction of an optical spacer between the transmitter and the tubing and the tubing and the receiver and with this markedly improved results were achieved.

Accordingly, the object of the present invention is achieved by providing a new and improved device for detecting the presence of air in translucent or transparent tubing, including a body providing accommodation for the tubing, a light energy transmitter for transmitting light energy towards the tubing and a light energy receiver for receiving light energy transmitted by the transmitter and modified by changes in the constituency of fluid passing through the tubing, wherein an optical spacer is provided occupying space between the light energy transmitter and the tubing and the tubing and the light energy receiver.

Preferably the light energy transmitter and the light energy receiver are operative in the infra-red spectrum, and preferably the transmitter is an LED (light emitting diode) and the receiver is a phototransistor.

Preferably the device includes a body having a passage therethrough for accommodating the tubing and the optical spacer is in the form of a collar within the passage and surrounding the tubing, the light energy transmitter and the light energy receiver being housed in the body.

Preferably the light energy transmitter and the light energy receiver are located in passages extending through the body and opening into the tubing accommodating passage.

Normally the transmitter and receiver locating passages open into the tubing accommodating passage via respective apertures. The apertures may be in fixed walls, integral with the body, which otherwise close the passages or in plugs inserted in the passages otherwise to close the same.

The apertures may be of different sizes chosen to provide optimum effect in any given device. Commonly, the aperture through which the transmitter communicates will be of smaller cross-sectional area than the aperture through which the receiver communicates. In one embodiment of the invention wherein the apertures are of circular cross-section, the diameter of the aperture through which the transmitter communicates is at least approximately half the diameter of the aperture through which the receiver communicates.

Preferably the transmitter and receiver are spaced around the tubing accommodating passage, preferably with their principle optic axes in the same transverse plane. Preferably again the transmitter and receiver are arranged with their principle optic axes orthogonal one to the other.

Where the axes lie in the same transverse plane it may be found that satisfactory results are obtained with the optic axes at some relative angle other than 90° but it is believed that optimum results are obtained when the axes are orthogonal one to the other. Again, spacing the transmitter and receiver along the length of the tubing accommodating passage may be found to give satisfactory results but arranging the transmitter and receiver such that their principle optic axes are spaced around the tubing accommodating passage is believed to provide optimum results.

The tubing used in the intravenous supply of fluids to a patient is of course of circular cross-section and normally therefore the tubing accommodating passage is of circular cross-section.

Typically the outer diameter of the tubing accommodating passage (and said collar) will be between twice and three times the outside diameter of said tubing. In a preferred embodiment the outer diameter of the tubing accommodating passage is 2.5 times the outer diameter of the tubing.

Preferably the transmitter and receiver are discrete devices and preferably an LED (light emitting diode) and a phototransistor, respectively. Normally such components are generally circular-cylindrical in overall outline and accordingly, the transmitter and receiver passages are normally circularly cylindrical.

In order to simplify the insertion and removal of the tubing, preferably the tubing accommodating passage has a linearly extending slot through which the tubing may be slotted and the collar is correspondingly gapped. The width of the slot and the width of the gap are not necessarily similarly dimensioned but it is convenient that that should substantially be so.

The material chosen for the optical spacer should be a reasonable match optically to the material of said tubing. Preferably the material is acrylic.

It should be noticed that whilst a device in accordance with the present invention is primarily intended to operate with tubing which is relatively large bored thin-walled tubing as used in the intravenous supply of fluids to a patient, it may be operable using small bore thick-walled tubing as used in clinical analysis although, as previously mentioned, the known device shown in FIG. 1 operates satisfactorily with such tubing.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 2:
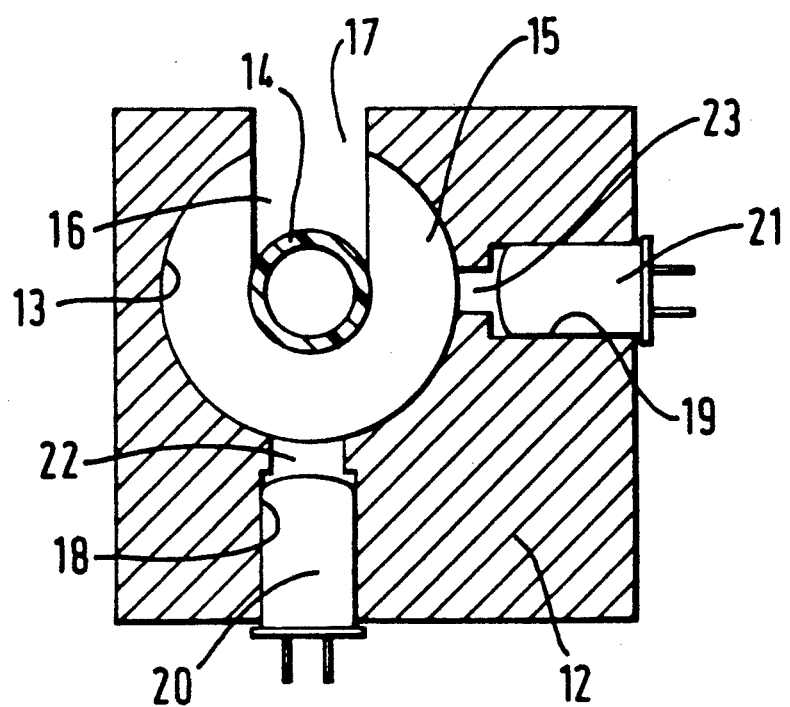
FIG. 2 is a transverse cross-sectional view of the device according to the present invention for detecting the presence of air in tubing forming part of a fluid flow system for the intravenous supply of fluid to a medical patient.

Referring now to the drawings, wherein like reference numerals designate identical or corresponding parts throughout the several views, and more particularly to FIG. 2 thereof, the device of the present invention includes a body member 12 having a passage 13 passing therethrough in which may be accommodated a length of transparent big bore thin-walled p.v.c. tubing 14. Tubing 14 has an internal diameter of 3.0 mm and an outside diameter of 4.1 mm. Passage 13 is of diameter 10 mm. Located within said passage 13 is a collar 15 of material chosen to be a good optical match with the material of the tubing 14. In this case the material of the collar 15 is acrylic. The collar 15 surrounds the tubing 14 save for a gap 16 which is of width sufficient for the tubing 14 to pass through. Gap 16 is aligned with a slot 17, of similar width, extending longitudinally through the top (as viewed) of the passage 13. The slot 17 and gap 16 enable the tubing 14 readily to be slotted into position and removed after use.

Extending into the body 12 from its base and right-hand side (as viewed) respectively are two circular-cylindrical passages 18 and 19 in which are located respectively an infra-red receiver 20 in the form of a phototransistor and an infra-red transmitter 21 in the form of an LED.

Circular-cylindrical passages 18, 19 are orthogonal to each other and exit via apertures 22, 23 respectively into tubing passage 13. The openings of apertures 22, 23 in tubing passage 13 are covered by the outer surface of optical spacer 15. In this particular example the receiver and transmitter apertures 22, 23 are not of the same diameter. The diameter of transmitter aperture 23 is one half that of receiver aperture 22.

Figure 1:
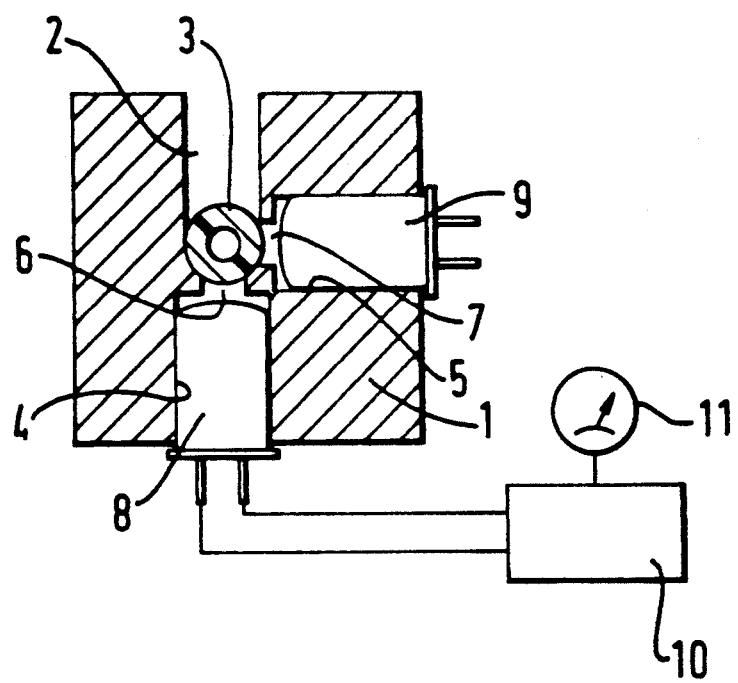
FIG. 1 is a cross-sectional view of a conventional device for detecting air in tubing.

With an arrangement as described above and utilizing for infra-red transmitter 21 a type TSTS 7202 LED and for infra-red receiver 20 a type BPW 77B and with receiver and transmitter apertures of diameter 3.0 mm and 1.5 mm respectively, a test corresponding to that described earlier in reference to FIG. 1 provided an indication of 0.3 volts when the fluid passage through tubing 14 was distilled water; 1.2 volts when the fluid was semi-skimmed milk; 1.2 volts when the fluid was a 20% intralipid solution and 4.0 volts when air passed through. It will be recalled that with an arrangement generally as illustrated in FIG. 1 but adapted dimensionally to accept relatively large bore, thin-walled tubing such as tubing 14 in FIG. 2 in contrast provided a change in output in the presence of air which was insufficiently marked to be useful in the terms of "air-in-line" detection.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A device for detecting the presence of air in translucent or transparent tubing, comprising:
    a body having a tubing accommodating passage providing accommodation for said tubing;
    a light energy transmitter for light transmitting light energy towards said tubing;
    a light energy receiver for receiving light energy transmitted by said transmitter and modified by changes in the constituency of fluid passing through said tubing; and
    an optical spacer having a circular cross-section and occupying space between said light energy transmitter and said tubing and said tubing and said light energy receiver in said tubing accommodating passage,
    wherein said light energy transmitter and said light energy receiver are located in passages extending through said body and opening into said tubing accommodating passage.

2. A device as claimed in claim 1, wherein said light energy transmitter and said light energy receiver are operative in the infra-red spectrum.

3. A device as claimed in claim 1, wherein said transmitter is an LED and said receiver is a phototransistor.

4. A device as claimed in claim 1, comprising:
said body having a passage therethrough for accommodating said tubing; and
said optical spacer being in the form of a collar within said passage and surrounding said tubing, said light energy transmitter and said light energy receiver being housed in said body.

5. A device as claimed in claim 1, wherein said transmitter and locating receiver passages open into said tubing accommodating passage via respective apertures.

6. A device as claimed in claim 5, wherein said apertures are in fixed walls, integral with said body, which otherwise close said passages.

7. A device as claimed in claim 6, wherein said apertures are in plugs inserted in said passages otherwise to close the same.

8. A device as claimed in claim 6, wherein said apertures are of different sizes.

9. A device as claimed in claim 8, wherein said aperture through which said transmitter communicates is of smaller cross-sectional area than the aperture through which said receiver communicates.

10. A device as claimed in claim 9, wherein said apertures are of circular cross-section, with the diameter of the aperture through which said transmitter communicates at least approximately half the diameter of the aperture through which said receiver communicates.

11. A device as claimed in claim 1, wherein said transmitter and receiver are spaced around said tubing accommodating passage.

12. A device as claimed in claim 11, wherein said transmitter and receiver have principle optic axes which lie in the same transverse plane.

13. A device as claimed in claim 1, wherein said transmitter and receiver have principle optic axes arranged orthogonal one to the other.

14. A device as claimed in claim 1, wherein said collar has an outer diameter between twice and three times the outside diameter of said tubing.

15. A device as claimed in claim 14, wherein the outer diameter of said collar is 2.5 times the outer diameter of said tubing.

16. A device as claimed in claim 1, wherein said optical spacer has a radially extending slot in which said tubing is disposed in intimate contact with said collar.

17. A device as claimed in claim 1, wherein the optical spacer is made of an acrylic material.

18. A device as claimed in claim 16, wherein said tubing is disposed in said slot coincident with a longitudinal axis of said collar, and said transmitter and receiver have principle optic axes arranged orthogonal to one another in a common transverse plane and intersecting said tubing.

19. A device according to claim 18, wherein the principle optic axes of said transmitter and said receiver intersect the longitudinal axis of said tubing.

20. A device for detecting the presence of air in translucent or transparent tubing, comprising:
a body providing accommodation for said tubing;
a light energy transmitter for light transmitting light energy towards said tubing;
a light energy receiver for receiving light energy transmitted by said transmitter and modified by changes in the constituency of fluid passing through said tubing; and
an optical spacer occupying space between said light energy transmitter and said tubing and said tubing and said light energy receiver, comprising a cylindrical element having a dielectric constant greater than that of air, said element having a tubing passage extending along a longitudinal axis of the cylindrical element and in which said tubing is disposed in intimate contact with said cylindrical element.

21. A device according to claim 20, wherein said tubing passage comprises a radially extending slot.

22. A device according to claim 20, wherein said transmitter and receiver have principle optic axes arranged orthogonal to one another in a common transverse plane and intersecting said tubing.

23. A device according to claim 21, wherein said transmitter and receiver have principle optic axes arranged orthogonal to one another in a common transverse plane and intersecting said tubing.

24. A device according to claim 21, wherein the principle optic axes of said transmitter and said receiver intersect the longitudinal axis of said tubing.

25. A device according to claim 23, wherein the principle optic axes of said transmitter and said receiver intersect the longitudinal axis of said tubing.

* * * * *